US011111201B2

(12) United States Patent
Blaude et al.

(10) Patent No.: US 11,111,201 B2
(45) Date of Patent: Sep. 7, 2021

(54) REDUCTION OF CONTENT OF CARBOXYLIC ACIDS AND DERIVATIVES THEREOF IN OLEUM, DISULFURIC ACID OR CONCENTRATED SULFURIC ACID

(71) Applicant: SOLVAY SA, Brussels (BE)

(72) Inventors: Jean-Marie Blaude, Brussels (BE); Benoit Gosselin, Ophain (BE); Alain Lambert, Beauvechain (BE); Matthias Marek, Offenau (DE); Harald Krueger, Bad Wimpfen (DE); Jan Schostag, Bad Rappenau (DE); Miriam Heyd, Bad Rappenau (DE)

(73) Assignee: Solvay SA, Brussels (BE)

( * ) Notice: Subject to any disclaimer, the term of this patent is extended or adjusted under 35 U.S.C. 154(b) by 0 days.

(21) Appl. No.: 16/607,846

(22) PCT Filed: Apr. 25, 2018

(86) PCT No.: PCT/EP2018/060549
§ 371 (c)(1),
(2) Date: Oct. 24, 2019

(87) PCT Pub. No.: WO2018/197539
PCT Pub. Date: Nov. 1, 2018

(65) Prior Publication Data
US 2020/0223778 A1    Jul. 16, 2020

(30) Foreign Application Priority Data

Apr. 26, 2017  (EP) .................................. 17168261

(51) Int. Cl.
*C07C 51/42* (2006.01)
*C01B 17/88* (2006.01)
*C01B 17/90* (2006.01)
*C07C 51/43* (2006.01)
*C07C 51/56* (2006.01)
*C07C 51/573* (2006.01)
*C07C 53/00* (2006.01)
*C07C 53/16* (2006.01)
*C07C 53/18* (2006.01)

(52) U.S. Cl.
CPC .............. *C07C 51/42* (2013.01); *C01B 17/88* (2013.01); *C01B 17/905* (2013.01); *C07C 51/43* (2013.01); *C07C 51/56* (2013.01); *C07C 51/573* (2013.01); *C07C 53/00* (2013.01); *C07C 53/16* (2013.01); *C07C 53/18* (2013.01)

(58) Field of Classification Search
None
See application file for complete search history.

(56) References Cited

U.S. PATENT DOCUMENTS

| 3,288,850 | A |   | 11/1966 | Nychka et al. |
| 5,164,049 | A | * | 11/1992 | Clark ....................... B01D 1/02 134/12 |
| 5,275,791 | A |   | 1/1994 | Mazzafro et al. |
| 6,583,327 | B2 | * | 6/2003 | Demuth ................ C07C 201/08 568/939 |

FOREIGN PATENT DOCUMENTS

| EP | 2 810 931 A1 | 12/2014 | |
| EP | 2810931 B * | 4/2018 | ............. C07C 51/56 |
| WO | WO-2014195929 A2 * | 12/2014 | ............. C07C 51/56 |

\* cited by examiner

*Primary Examiner* — Amy C Bonaparte
(74) *Attorney, Agent, or Firm* — Osha Bergman Watanabe & Burton LLP

(57) ABSTRACT

The present invention concerns a process for the reduction of content of carboxylic acids and derivatives thereof in oleum, disulfuric acid or concentrated sulfuric acid. The invention further concerns a process for the manufacture of carboxylic acid anhydrides comprising the process for the reduction of content of carboxylic acids and derivatives thereof from oleum, disulfuric acid or concentrated sulfuric acid.

16 Claims, No Drawings

REDUCTION OF CONTENT OF CARBOXYLIC ACIDS AND DERIVATIVES THEREOF IN OLEUM, DISULFURIC ACID OR CONCENTRATED SULFURIC ACID

This application is a U.S. national stage entry under 35 U.S.C. § 371 of International Application No. PCT/EP2018/060549 filed Apr. 25, 2018, which claims priority to European application No. 17168261.0, filed on Apr. 26, 2017. The entire contents of these applications are explicitly incorporated herein by this reference.

This application claims priority to European application No. 17168261.0, the whole content of this application being incorporated herein by reference for all purposes.

The present invention concerns a process for the reduction of content of carboxylic acids and derivatives thereof in oleum, disulfuric acid or concentrated sulfuric acid. The invention further concerns a process for the manufacture of carboxylic acid anhydrides comprising the process for the reduction of content of carboxylic acids and derivatives thereof from oleum, disulfuric acid or concentrated sulfuric acid.

Carboxylic anhydrides, in particular halogenated carboxylic anhydrides like trifluoroacetic acid, are valuable reagents for the manufacture of various products in the pharmaceutical and agrochemical industry.

It is known from EP2810931 that carboxylic anhydrides, in particular halogenated carboxylic anhydrides, can be manufactured by reaction of the corresponding carboxylic acid with oleum, disulfuric acid or concentrated sulfuric acid. Necessarily, the oleum, disulfuric acid or concentrated sulfuric acid can get contaminated with carboxylic anhydride, carboxylic acid and/or derivatives thereof. Depending on the further application of the oleum, disulfuric acid or concentrated sulfuric acid, these contaminations can be undesirable, for example when oleum, disulfuric acid or concentrated sulfuric acid are recycled or subjected to scrubber or waste water treatment. Especially halogenated caboxylic acids or their derivatives can create problem in waste water treatment, resulting in costly post manufacturing treatment.

Therefore, the present invention makes available a process the reduction of content of carboxylic acids and derivatives thereof in oleum, disulfuric acid or concentrated sulfuric acid. The process makes manufacturing methods by which oleum, disulfuric acid or concentrated sulfuric acid a generated which comprise carboxylic acids, in particular halogenated carboxylic acids, and derivatives thereof more economical by avoiding laborious post manufacturing treatments of the contaminated oleum, disulfuric acid or concentrated sulfuric acid redundant. The process renders such processes not only economically more viable, but also often creates less toxic effluents and/or is less harmful to the environment. The oleum, disulfuric acid or concentrated sulfuric acid subjected to the process for the reduction of content of carboxylic acids and derivatives thereof can also be more economically recycled, if desired, without build up of contaminants.

Accordingly, the invention concerns a process for the reduction of content of carboxylic acids and derivatives thereof in oleum, disulfuric acid or concentrated sulfuric acid, which comprises submitting a first fraction of comprising oleum, disulfuric acid or concentrated sulfuric acid with a first content of carboxylic acid or at least one derivative thereof to a gas stripping operation in order to obtain a second fraction comprising oleum, disulfuric acid or concentrated sulfuric acid with a second content of carboxylic acid or at least one derivative thereof, wherein the second content of carboxylic acid or at least one derivative thereof in the second fraction comprising oleum, disulfuric acid or concentrated sulfuric acid is lower than the first content in the first fraction. The invention further concerns a process for the manufacture of a carboxylic acid anhydride comprising a step of reacting a compound of formula (III) $R_3C(O)OH$, wherein R independently is selected from the group consisting of H, F, Cl, Br, alkyl and aryl, with sulfuric acid, oleum and/or disulfuric acid, and which further comprises the process for the reduction of content of carboxylic acids and derivatives thereof in oleum, disulfuric acid or concentrated sulfuric acid. Another object of the present invention is a process for the manufacture of an agrochemically or pharmaceutically active compound, which comprises the process for the reduction of content of carboxylic acids and derivatives thereof in oleum, disulfuric acid or concentrated sulfuric acid.

In the present invention, designations in singular are in intended to include the plural; for example, "a carboxylic acid" is intended to denote also "more than one carboxylic acid" or "a plurality of carboxylic acids".

All aspects and embodiments of the present invention are combinable.

In the context of the present invention, the term "comprising" is intended to include the meaning of "consisting of".

In a first embodiment, the invention concerns a process for the reduction of content of carboxylic acids and derivatives thereof in a fraction comprising oleum, disulfuric acid or concentrated sulfuric acid, which comprises submitting a first fraction comprising oleum, disulfuric acid or concentrated sulfuric acid with a first content of carboxylic acid or at least one derivative thereof to a gas stripping operation in order to obtain a second fraction comprising oleum, disulfuric acid or concentrated sulfuric acid with a second content of carboxylic acid or at least one derivative thereof, wherein the second content of carboxylic acid or at least one derivative thereof in the second fraction comprising oleum, disulfuric acid or concentrated sulfuric acid is lower than the first content. The expression "second content of carboxylic acid or at least one derivative thereof in the second fraction comprising oleum, disulfuric acid or concentrated sulfuric acid is lower than the first content" intends to denote that the content of carboxylic acid or at least one derivative thereof in the fraction comprising oleum, disulfuric acid or concentrated sulfuric acid is reduced by the stripping operation. Often, the first content is from 1 to 15 or 1 to 10 wt % of carboxylic acid and/or derivative thereof. The second content often is from 0, thus, below detection by GC or IC (ion chromatography), to 2 wt % of carboxylic acid and/or derivative thereof. Often, values of the second content of from 0.01 to 0.1 wt % can be achieved.

The term "sulfuric acid" is intended to denote sulfuric acid, $H_2SO_4$, as well as aqueous solutions thereof. Generally, the sulfuric acid has a concentration of equal to or more than 20%. Concentrations of equal to or more than 30% or 50% can also be employed. Preferably, the sulfuric acid in the first fraction according to this invention has a concentration of equal to or more than 70 wt % and above, more preferably a concentration of equal to or more than 90 wt %, and most preferably concentrated sulfuric acid is used, which has a concentration of equal to or more than 95 wt % or even 98 wt %.

The term "oleum" is intended to denote mixtures of $H_2SO_4$ and $SO_3$. Concentrations of oleum are either expressed in terms of wt % $SO_3$ (called X % oleum) or as wt % $H_2SO_4$. For example, 65% oleum refers to 114.6 wt % $H_2SO_4$. The percentage of $SO_3$ in the oleum is also referred to as the free $SO_3$. Thus, 65% oleum contains 65 wt % free $SO_3$.

The term "disulfuric acid" is intended to denote $H_2S_2O_7$.

The term "stripping operation" denotes the introduction of a gas stream into a liquid volume containing a mixture of at least two substances of differing volatility. The term "stripping" also includes the terms sparging, bubbling or gas flushing. Generally, the at least one substance whose content is reduced by stripping out of a fraction a mixture of at least two substances of differing volatility possesses a higher volatility than at least one other substance remaining in the liquid phase. In this case, it has been shown that suprisingly, the content of carboxylic acids and derivatives comprised in a fraction of of oleum, disulfuric acid or concentrated sulfuric acid can be reduced by a stripping operation.

In one aspect carboxylic acid or carboxylic acid anhydride or carboxylic acid and carboxylic acid anhydride is comprised in the first fraction comprising oleum, disulfuric acid or concentrated sulfuric acid.

The carboxylic acid or its derivative preferably is a halogenated carboxylic acid or its derivative, wherein the halogenated carboxylic acid is a compound of formula (I) $HalR_2C$—$C(O)$—$OH$, wherein Hal is selected from the group consisting of F, Cl and Br, and wherein R is independently selected from the group consisting of H, F, Cl, Br, alkyl and aryl. The term "alkyl" is intended to denote an optionally substituted chain of saturated hydrocarbon-based groups, such as, in particular, a $C_1$-$C_6$ alkyl. By way of example, mention may be made of methyl, ethyl, propyl, isopropyl, t-butyl, butyl, pentyl, isopentyl and hexyl. The alkyl group can optionally be substituted. The term "aryl" is intended to denote an optionally substituted group which derives from an aromatic nucleus such as, in particular, a $C_6$-$C_{10}$ aromatic nucleus, in particular phenyl or naphthyl. The aryl group can optionally be substituted. Derivatives of carboxylic acid can be, for example, carboxylic acid anhydride, or reaction products obtained by reaction of oleum, disulfuric acid or concentrated sulfuric acid with carboxylic acid, for example esters and anhydrides of carboxylic acid and oleum, disulfuric acid or concentrated sulfuric acid.

In a preferred aspect, Hal is F in the compound according to formula (I). More preferably, the compound of formula (I) is trifluoroacetic acid.

In another aspect, the derivative of the carboxylic acid which can be comprised in the first fraction is a carboxylic acid anhydride. Preferably, the carboxylic acid anhydride comprised in the first fraction is a compound of formula (II) $HalR_2C$—$C(O)$—$O$—$C(O)CR_2Hal$, wherein Hal and R are defined as above, preferably the compound of formula (II) is trifluoroacetic acid anhydride.

The oleum often contains from 5 to 95 wt % free $SO_3$, preferably from 25 to 80 wt % free $SO_3$, more preferably from 50 to 70 wt % free $SO_3$, most preferably 65 wt % free $SO_3$.

The stripping operation according to the present invention generally is performed using at least one gas selected from the group consisting of air, oxygen, $CO_2$, exhaust gas, and inert gases, preferably helium, nitrogen, argon or xenon. Nitrogen is preferred. Gas mixtures of two or more of the foregoing gases are also suitable. The stripping operation according to the present invention is performed in an apparatus suitable for a gas stripping operation. In one preferred aspect, the stripping is performed by introduction of the stripping gas into the first fraction by subsurface dip pipe. The first fraction is provided in a vessel suitable for containing the first fraction selected according to the first fraction's corrosivity and necessary temperature. The vessel can, for example, be at least partially ceramic-lined and/or a glass-lined. Suitably, a continuously-stirred Pfaundler vessel with a ceramic lining can be used. Also preferably, the process can be performed in a reaction vessel at least partially made of an alloy containing nickel and/or molybdenum. Examples of suitable alloys include Hastelloy B, Hastelloy B-2, or Hastelloy B-3. In another preferred stripping system, gas diffusers are placed near the bottom of a reservoir containing the first fraction, introducing the stripping gas below the surface of the first fraction. Other apparatus can also be selected for the stripping operation as long as the material is compatible with the first fraction; such apparatus includes, but is not limited to, packed tower strippers, bubble tray tower, diffused gas (aeration) strippers, tray strippers or mechanical strippers such as the Hazleton Maxi-strip® System. Depending on the stripping apparatus, the stripping gas or stripping gas mixture can also be introduced to the first fraction by introducing the first fraction descending over porous packings, wherein the gas is blown through the packing pores, stripping off the volatile compounds. The stripping operation can be performed continuously, in a countercurrent or co-current way, or batchwise. In one preferred aspect, the stripping is performed in a bubble tray tower wherein the first fraction is fed top to bottom, and the stripping gas, preferably air or nitrogen, is fed countercurrent. The efficiency of reducing the content of carboxylic acids and derivatives, is suitably measured by methods known to the person skilled in the art, for example GC or IC, using calibration with an external standard, or titration.

According to the present invention, the stripping operation is generally performed at temperatures of from 10 to 160° C. Generally, the temperature of the first fraction in the stripping step is equal to or higher than 10° C. More preferably, the temperature of the first fraction in the stripping step is equal to or higher than 15° C. Most preferably, temperature of the first fraction in the stripping step is equal to or higher than 20° C. Generally, the temperature of the first fraction in the stripping step is equal to or lower than 160° C. Preferably, the temperature of the first fraction in the stripping step is equal to or lower than 140° C. At temperature of equal to or lower than 120° C. or 100° C. can be preferred. In a most preferred aspect of the invention, the temperature of the first fraction in the stripping step is from 100° C. to 140° C.

In a preferred aspect of the present invention, the stripping operation is performed at ambient pressure, which generally is a value of from 950 mbar to 1150 mbar absolute. In another aspect of the invention, the pressure in the stripping apparatus is controlled in a selected pressure range. Pressures below or above ambient pressure can be employed. In one aspect of the invention, the pressure in the stripping apparatus is from 50 to 500 mbar. Often, the pressure in the stripping apparatus is equal to or more than 50 mbar. More preferably, the pressure in the stripping apparatus is equal to or more than 100 mbar. Most preferably, the pressure in the stripping apparatus is equal to or more than 150 mbar. Often, the pressure in the stripping apparatus is equal to or lower than 600 mbar. More preferably, the pressure in the stripping apparatus is equal to or lower than 550 mbar. Most preferably, the pressure in the stripping apparatus is equal to or lower than 500 mbar. In another aspect of the present invention, the stripping operation can be performed at a pressure above ambient pressure, for example at a pressure of from more than 1050 mbar to 1250 mbar.

According to the present invention, the process for the reduction of content of carboxylic acids and derivatives thereof in oleum, disulfuric acid or concentrated sulfuric acid can further comprises an additional separation step, preferably a distillation step, prior to the gas stripping operation, in order to effect a first reduction of the content of carboxylic acids and derivatives in the first fraction.

In one aspect, it can be advantageous to dilute the first fraction comprising oleum with an aqeuous phase, preferably water, in order to obtain a first fraction of concentrated sulfuric acid before the stripping operation. This reduces or eliminates the risk of loss of temperature due to stripping of $SO_3$ our of the system, which would unduly impact the heat efficiency of the process and might lead to freezing of stripped $SO_3$ on the cooling equipments.

The amount of gas introduced into the first fraction during the stripping operation per time interval is selected appropriately in order to obtain a good result of reduction of content of carboxylic acids and derivatives in the fraction, while sputtering and overly heat loss is avoided. Depending on the volume of the first fraction and/or the apparatus used, a gas flow of from 1 to 10 $m^3/h$ often is suitable. In a preferred aspect, a gas flow rate of about 5 $m^3/h$ can be selected.

The invention concerns further a process for the manufacture of a carboxylic acid anhydride comprising a step of reacting a compound of formula (III) $R_3C$—$C(O)OH$, wherein R independently is selected from the group consisting of H, F, Cl, Br, alkyl and aryl, with sulfuric acid, oleum and/or disulfuric acid, and which further comprises the process for the reduction of content of carboxylic acids and derivatives thereof in oleum, disulfuric acid or concentrated sulfuric acid, as described above. Preferably, the compound of formula (HU is a compound of formula (I) $HalR_2C$—$C(O)$—$OH$, wherein Hai and R are defined as before, wherein Hal most preferably is F. Suitable processes are disclosed, for example, in EP2810931, whose content is hereby included by reference for all purposes.

Another object of the present invention is a process for the manufacture of an agrochemically or pharmaceutically active compound, which comprises at least one step in which an agrochemically or pharmaceutically active compound or precursor thereof is manufactured. Wherein the at least one step generates a fraction of oleum, disulfuric acid or concentrated sulfuric acid having a content of carboxylic acids. The process further comprises the process for the reduction of content of carboxylic acids and derivatives thereof in oleum, disulfuric acid or concentrated sulfuric acid, as described above. In such as process, it is possible to manufacture an agrochemically or pharmaceutically active compound or an intermediate thereof while being able to effectively recycle and/or manage fractions and waste streams of oleum, disulfuric acid or concentrated sulfuric acid by reducing the content of carboxylic acids in such a process for manufacturing, the agrochemically or pharmaceutically active compound or its intermediate. This concerns in particular a process for the manufacture of an agrochemically or pharmaceutically active compound which comprises the process for the manufacture of a carboxylic acid anhydride comprising a step of reacting a compound of formula (III) $R_3C$—$C(O)OH$ with oleum, disulfuric acid or concentrated sulfuric acid, which often generates fractions of oleum, disulfuric acid or concentrated sulfuric acid with a content of carboxylic acids which need to be recycled or submitted to waste management, and wherein the organic freight (carboxylic acids) can be considered to be detrimental. It is known, for example, that trifluoro acetic acid anhydride is a suitable building block for agrochemical compounds comprising a $CF_3$ group, such as, for example, flonicamid car pyroxysulfone. Trifluoro acetic acid anhydride can be made from trifluoro acetic acid by reacting trifluoro acetic acid with sulfuric acid, oleum and/or disulfuric acid, which generates a fraction of sulfuric acid, oleum and/or disulfuric acid which comprises trifluoroacetic acid.

The process of the present invention effectively reduces the content of carboxylic acids and derivatives thereof in the second fraction obtained by the process comprising oleum, disulfuric acid or concentrated sulfuric acid. The resulting fraction can be better recycled or disposed of without undue environmental impact or necessity of laborious post-production treatment. The effect is unexpected, as it was not foreseen that carboxylic acids and derivatives could be stripped from such a fraction, and as it was anticipated that by-products and effect solution of the carboxylic acids and derivatives, in particular those of halogenated carboxylic acids, would make a reduction by stripping operation impossible or ineffective.

Should the disclosure of any patents, patent applications, and publications which are incorporated herein by reference conflict with the description of the present application to the extent that it may render a term unclear, the present description shall take precedence.

The following examples are intended to further explain the invention without limiting it.

EXAMPLE 1

A first fraction of 98% $H_2SO_4$, obtained by the reaction of $CF_3COOH$ to $CF_3C(O)$—$O$—$C(O)CF_3$, manufactured by a procedure similar to the procedure described in EP2810931, after a reduction of $CF_3COOH$ by distillation and dilution of the oleum sump to 98% $H_2SO_4$ in the ceramic lined Pfaudler reaction vessel, was fitted with a subsurface dip pipe. The fraction comprised 2.8% $CF_3COOH$ (TFA) as measured by IC. At a temperature of approximately 130° C., a nitrogen flow of about 5 $m^3/h$ was introduced into the fraction. The results of the reduction of content of $CF_3COOH$ (TFA) in the fraction as measured by IC are given in the table below:

| TFA [%] | Elapsed time |
| --- | --- |
| 2.8 | 0:00:00 |
| 2.2 | 4:00:00 |
| 0.78 | 6:00:00 |
| 0.33 | 8:00:00 |
| 0.08 | 12:00:00 |
| 0.03 | 16:00:00 |

The resulting fraction was suitable to be submitted to conventional waste water treatment without additional treatment necessary for any freight of organic $CF_3$ contaminants. The gas flow emerging from the stripping operation was submitted to a scrubber cascade alternating equipped with an aqueous solution of KOH and $H_2O_2$.

The invention claimed is:

1. A process for the reduction of a content of carboxylic acids and derivatives thereof in oleum, disulfuric acid or sulfuric acid, the process comprising submitting a first fraction comprising oleum, disulfuric acid or sulfuric acid with a first content of carboxylic acid or at least one anhydride derivative thereof to a gas stripping operation in order to obtain a second fraction comprising oleum, disulfuric acid or sulfuric acid with a second content of carboxylic acid or at least one anhydride derivative thereof, wherein the second content of carboxylic acid or at least one anhydride derivative thereof in the second fraction comprising oleum, disulfuric acid or sulfuric acid is lower than the first content of carboxylic acid or at least one anhydride derivative thereof in the first fraction comprising oleum, disulfuric acid or sulfuric acid, wherein the carboxylic acid and/or carboxylic acid anhydride derivative of the first content is a halogenated carboxylic acid of formula (I) $HalR_2C\text{—}C(O)\text{—}OH$, wherein Hal is selected from the group consisting of F, Cl and Br, and wherein R is independently selected from the group consisting of H, F, Cl, Br, alkyl, and aryl, or a halogenated carboxylic acid anhydride derivative thereof.

2. The process according to claim 1, wherein Hal is F.

3. The process according to claim 2, wherein the compound of formula (I) is trifluoroacetic acid.

4. The process according to claim 1, wherein the halogenated carboxylic acid anhydride derivative is a compound of formula (II) $HalR_2C\text{—}C(O)\text{—}OC(O)CR_2Hal$, wherein Hal is selected from the group consisting of F, Cl and Br, and wherein R is independently selected from the group consisting of H, F, Cl, Br, alkyl and aryl.

5. The process according to claim 1, wherein the oleum contains from 5 to 95 wt % free $SO_3$.

6. The process according to claim 1, wherein the sulfuric acid has a concentration of equal to or more than 20 wt %.

7. The process according to claim 1, wherein the gas stripping operation is performed using at least one gas selected from the group consisting of air, oxygen, $CO_2$, exhaust gas, and inert gases.

8. The process according to claim 1, wherein the gas stripping operation is performed continuously in a countercurrent or co-current way, or batchwise in a countercurrent or co-current way.

9. The process according to claim 1, wherein the first fraction submitted to the gas stripping operation has a temperature of from 10 to 160° C. in the gas stripping operation.

10. The process according to claim 1, wherein the stripping operation is performed at a pressure of from 50 to 500 mbar.

11. A process for the manufacture of a carboxylic acid anhydride comprising a step or reacting a compound of formula (I) $HalR_2C\text{—}C(O)\text{—}OH$, wherein Hal is selected from the group consisting of F, Cl, and Br, and wherein R is independently selected from the group consisting of H, F, Cl, Br, alkyl, and aryl, with sulfuric acid, oleum and/or disulfuric acid, and which further comprises the process according to claim 1.

12. The process according to claim 4, wherein the compound of formula (II) is trifluoroacetic acid anhydride.

13. The process according to claim 5, wherein the oleum contains from 25 to 80 wt % free $SO_3$.

14. The process according to claim 13, wherein the oleum contains from 50 to 70 wt % free $SO_3$.

15. The process according to claim 7, wherein the inert gases comprise helium, nitrogen, argon, or xenon.

16. The process according to claim 13, wherein Hal is F.

* * * * *

UNITED STATES PATENT AND TRADEMARK OFFICE
CERTIFICATE OF CORRECTION

| | |
|---|---|
| PATENT NO. | : 11,111,201 B2 |
| APPLICATION NO. | : 16/607846 |
| DATED | : September 7, 2021 |
| INVENTOR(S) | : Jean-Marie Blaude et al. |

It is certified that error appears in the above-identified patent and that said Letters Patent is hereby corrected as shown below:

In the Claims

In Claim 16, Column 8, Line 29, the phrase "claim 13" should read -- claim 11 --

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*